United States Patent [19]

Tuttle

[11] Patent Number: 4,562,206

[45] Date of Patent: Dec. 31, 1985

[54] ORALLY EFFECTIVE INOTROPIC COMPOUNDS

[75] Inventor: Ronald R. Tuttle, Plantation, Fla.

[73] Assignee: Key Pharmaceuticals, Inc., Miami, Fla.

[21] Appl. No.: 587,444

[22] Filed: Mar. 8, 1984

Related U.S. Application Data

[63] Continuation of Ser. No. 564,858, Dec. 23, 1983, abandoned.

[51] Int. Cl.$^4$ .................. C07C 103/29; C07C 69/017; A61K 31/165; A61K 31/225
[52] U.S. Cl. .................... 514/548; 514/620; 560/142; 564/165
[58] Field of Search ............... 514/548, 620; 564/165; 560/251, 142

[56] References Cited

U.S. PATENT DOCUMENTS

| | | | |
|---|---|---|---|
| 3,803,230 | 4/1974 | Jack et al. ........................... | 564/165 |
| 3,816,516 | 6/1974 | Cox et al. ......................... | 260/501.17 |
| 3,845,123 | 10/1974 | Cox et al. ......................... | 564/165 X |
| 3,987,200 | 10/1976 | Tuttle et al. ........................ | 424/330 |
| 4,086,272 | 4/1978 | Cox et al. ......................... | 260/559 D |
| 4,218,470 | 8/1980 | Casegrande et al. ............ | 560/142 X |
| 4,311,706 | 1/1982 | Bodor et al. ..................... | 564/165 X |
| 4,340,603 | 7/1982 | Bodor et al. ..................... | 424/301 |
| 4,396,627 | 8/1983 | Ainsworth et al. ............. | 560/251 X |

Primary Examiner—Thomas A. Waltz
Attorney, Agent, or Firm—Wegner & Bretschneider

[57] ABSTRACT

A method for increasing cardiac contractility in a warm-blooded animal suffering from acutely depressed cardiac contractility which comprises administering to said animal an effective amount of a compound of the formula

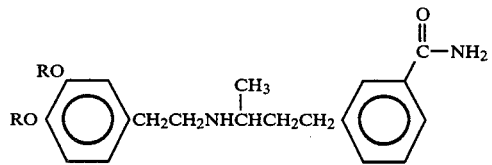

wherein R is hydrogen or isobutyrate, or a pharmaceutically acceptable acid addition salt thereof.

12 Claims, 4 Drawing Figures

FIGURE 2

FIGURE 3

ORALLY EFFECTIVE INOTROPIC COMPOUNDS

This application is a continuation of my application Ser. No. 564,858, filed Dec. 23, 1983, now abandoned.

Dobutamine (Tuttle and Mills, U.S. Pat. No. 3,987,200) has proven to be an effective inotropic agent for the treatment of heart failure (Circulation 56: 468, 1977). However, only a patient who has been intravenously catheterized is able to benefit from dobutamine treatment because the drug must be given by constant intravenous infusion, and the patient's pressure must be continuously monitored during administration. Thus, this mode of administration requires the close supervision of medical personnel that are usually available only in a hospital. Routes of administration other than constant intravenous infusion have not been feasible with dobutamine because it is rapidly cleared from the blood.

Although the intravenous route of administration greatly limits the number of patients who can benefit from dobutamine, the pharmacologic profile of dobutamine's actions is particuarly desirable. That is, dobutamine is cardioselective in its actions (Tuttle and Mills, Circ. Res. 36: 185, 1975). The importance of cardioselectivity is that a considerable increase in the heart's contractile performance (inotropic effect) can be obtained without causing an untoward increase or decrease in blood pressure. Lack of side effects on blood pressure is of particular importance because even a small deviation in blood pressure in patients with heart failure can produce disastrous effects.

Dobutamine's cardioselectivity results from its greater activity at the cardiac beta$_1$ adrenergic receptors than its activity at vascular alpha and beta$_2$ adrenergic receptors. Activity at beta$_1$ receptors produces the desired inotropic effect i.e. increasing cardiac contractility. Activity at vascular alpha receptors produces the undesirable side effect of increasing vascular resistance. Activity at either the vascular alpha or beta$_2$ receptor tends to decrease blood flow to vital visceral organs such as the kidneys. Alpha mediated vasoconstriction directly shuts down blood flow to these vital organs because there is a high density of alpha receptors in the vasculature of these organs. The density of beta$_2$ vascular receptors which mediate vasodilitation is low in vital visceral organs (e.g. kidney, liver and GI tract) and is high in skeletal muscle. Consequently a drug with high beta$_2$ activity dilates the vasculature of skeletal muscle and so causes a redistribution of blood flow toward skeletal muscle and away from vital organs.

In addition to the adverse side effects on the distribution of blood flow, activity at vascular alpha receptors causes abnormal increases in arterial blood pressure, and activity at vascular beta$_2$ receptors causes abnormal decrease in arterial blood pressure. Changes in blood pressure in either direction will exacerbate heart failure. A rise in blood pressure elevates the workload on the heart because the pressure that the heart must overcome to pump blood into the arterial system is elevated. On the other hand if the blood pressure is reduced below normal the pressure required to propel blood through the heart's coronary arteries becomes inadequate. Such a fall in coronary perfusion pressure can severely decrease myocardial bloodflow when the heart's coronary arteries are diseased. A blood flow decrease results in further impairment of the heart's contractile and thus pumping performance.

A drug that retains the cardioselective pharmacological profile of dobutamine, but that could be administered by routes other than by constant intravenous infusion, would be of considerable therapeutic benefit. Such a drug would bring to patients, suffering from heart failure, inotropic therapy as effective as that of dobutamine but without requiring hospitalization.

It has now been discovered that a rather specific alteration of dobutamine's chemical structure results in a new entity that suprisingly is effective orally, when swallowed or applied to and absorbed through the mouth's buccal mucosa, without sacrifice of dobutamine's cardioselectivity. It has also been discovered that by using a specific ester derivative of the new entity, absorption through the buccal mucosa is further enhanced.

Accordingly, the present invention provides novel compounds of the formulae and their pharmaceutically acceptable acid addition salts.

In another embodiment, the invention is a method for increasing cardiac contractility in a warm-blooded animal suffering from depressed cardiac contractility which comprises administering to said animal an effective amount of a compound of the formula wherein R is hydrogen or isobutyrate, or a pharmaceutically acceptable acid addition salts thereof. In more specific embodiments, the compound is administered orally or buccally.

The compounds according to the present invention can be prepared more conveniently by the reaction of an oxygen-protected 3,4-dihydroxyphenethylamine with the appropriate ketone to obtain a Schiff base and then reducing the base. For example, 3,4-dibenzyloxyphenethylamine and 3-(3'-oxobutyl)benzamide are condensed in an organic solvent usually in the presence of an acidic catalyst such as p-toluenesulfonic acid. The resultant imine or Schiff base using hydrogen or metal hydrides. Compound (I) can also be obtained in a single step when 3,4-dibenzyloxyphenethylamine and 3-(3'-oxobutyl)benzamide are reacted in an alcohol such as methanol or ethanol in the presence of sodium cyanoborohydride.

The diisobutyrate ester of Compound I is prepared from Compound I by conventional esterification procedures. For example, compound (I) is acylated with isobutyryl chloride in trifluoroacetic acid.

The present invention also contemplates pharmaceutically acceptable addition salts of the catechol and diisobutyryl ester amino compounds described herein. By "pharmaceutically acceptable salt," there are intended the conventional acid addition salts formed e.g., from pharmaceutically acceptable inorganic or organic acids. For example, such conventional salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic salicyclic, sulfanilic, fumaric, oxalic, toluenesulfonic, and the like.

The pharmaceutically acceptable salts of the present invention can be synthesized by conventional chemical methods. Generally, the salts are prepared by reacting the free base with stoichiometric amounts of with an excess of the desired salt forming inorganic or organic acid in a suitable solvent or various combinations of solvents. For example, the free base can be dissolved in a mixed aqueous solution of the appropriate acid and the salt recovered by standard techniques, for example, by evaporation of the solution. Alternatively, the free base can be charged into an organic solvent such as a lower alkanol, a symmetrical or asymmetrical ether containing 2 to 10 carbon atoms, an alkyl ester, or mixtures thereof, and the like, and then it is treated with the appropriate acid to form the corresponding salt. The salt is recovered by standard recovery techniques, for example, by filtration of the desired salt or spontaneous separation from the solution, or it can be precipitated by the addition of a solvent in which the salt is insoluble and recovered therefrom.

The present invention is described in more detail by way of the following non-limiting examples:

SYNTHESIS OF COMPOUNDS

Example 1

12.6 g of sodium hydride (50% oil) was washed three times each with 100 ml of n-hexane and suspended in 200 ml of N,N-dimethylformamide, with agitation while cooling to $-20°$ C. in a dry ice-ethanol bath. Into the suspension was gradually added dropwise 160 ml of ethyl acetoacetate. After generation of hydrogen had stopped, a solution of 49.0 g of m-cyanobenzyl bromide in 200 ml of N,N-dimethylformamide was added. The temperature was brought to room temperature and the reaction mixture allowed to stand overnight. After distilling off the solvent, the residue was extracted with ethyl acetate and the organic phase washed with a saturated saline solution and dried with anhydrous magnesium sulfate. The ethyl acetate was distilled off and the residue distilled to obtain 49.8 g of ethyl 2-(3'-cyanophenylmethyl)-3-oxobutyrate, boiling point 173° C./3 mmHg.

Example 2

38.2 g of ethyl 2-(3'-cyanophenylmethyl)-3-oxobutyrate was heated for 2 hours under reflux in 500 ml of concentrated hydrochloric acid. To the reaction solution was added 500 ml of water, followed by extraction three times with 500 ml portions of ethyl acetate. The organic phase was washed with water and dried with anhydrous sodium sulfate, after which the solvent was distilled off. The resultant 3-(3'-oxobutyl)benzoic acid was admixed with 500 ml of benzene and 17 ml of thionyl chloride and heated for 2 hours under reflux. The reaction solution was dropped into ice-cooled concentrated ammonia water and the resultant amide extracted three times with 500 ml portions of ethyl acetate. The organic phase was washed with a saturated saline solution and dried with anhydrous sodium sulfate. The solvent was distilled off and the residue recrystallized from ethyl acetate-n-hexane to obtained 23.1 g of 3-(3'-oxobutyl)benzamide, melting point 122°–125° C.

Example 3

2.61 g of 3,4-dibenzyloxyphenethylamine hydrochloride and 2.70 g of 3-(3'-oxobutyl)benzamide were dissolved in 50 ml of methanol, to which was added 0.47 g of sodium cyanoborohydride. The reaction was allowed to stand at room temperature for 15 hours. Then, the solvent was distilled off and the residue was extracted with 300 ml of ethyl acetate. The organic phase was washed with water and dried with anhydrous sodium sulfate. The solvent was distilled off and the residue was subjected to silica gel chromatography (solvent chloroform:ethanol:acetic acid=90:8:2) to obtain 2.91 g of N-[2-(3,4-dibenzyloxyphenyl)ethyl]-1-methyl-3-(3-carbamoylphenyl)propylamine as a viscous oil.

Example 4

2.91 g of N-[2-(3,4-dibenzyloxyphenyl)ethyl]-1-methyl-3-(3-carbamoylphenyl)propylamine was dissolved in 200 ml of ethanol, to which was added 0.3 g of palladium black. The reaction mixture was agitated at room temperature for 4 hours in a stream of hydrogen. The catalyst was separated and the solvent distilled off. The resultant residue was subjected to chromatography (solvent chloroform:methanol:acetate acid=80:17:3) and treated with 20% hydrogen chloride-ethanol, to obtain 1.15 g of N-[2-(3,4-dihydroxyphenyl)ethyl]-1-methyl-3-(3-carbamoylphenyl)propylamine hydrochloride as a powder.

| Elementary Analysis | C | H | N | Cl |
| --- | --- | --- | --- | --- |
| Calculated for $C_{19}H_{25}O_3N_2Cl \cdot H_2O$ | 59.60 | 7.11 | 7.32 | 9.26 |
| Found | 59.30 | 6.98 | 7.08 | 9.21 |

Example 5

4.1 g of N-[2-(3,4-dihydroxyphenyl)ethyl]-1-methyl-3-(3-carbamoylphenyl)propylamine hydrochloride was dissolved in 60 ml of trifluoroacetic acid to which was added 8.6 g of isobutyryl chloride, and stirred for 4 hours at room temperature. After completion of the reaction, the trifluoroacetic acid was distilled off under reduced pressure and the resulting residue was subjected to further silica gel chromatography. The solvent was first eluted by the use of chloroform and the reaction product was then eluted with a mixture of chloroform and methanol (90:10 by volume). The eluate containing the reaction product was concentrated to obtain an oily substance, which was then subjected to the silica gel chromatography [solvent chloroform:methanol=90:10 (by volume)] for purification. The solvent was distilled off to obtain a viscous oil. The oil was treated with ethyl acetate-$K_2CO_3$-water and the ethyl acetate phase separated. The ethyl acetate phase was washed with a saline solution and dried with anhydrous sodium sulfate, and the ethyl acetate was removed by distillation. The residue was dissolved in 5 ml of ethanol, to which were added 3.3 ml of 25% HCl-ethanol solution and then ethyl ether. The resultant oily substance was separated by decantation and washed with ether and dried under reduced pressure to obtain 3.0 g of powdery N[2-(3,4-diisobutyryloxyphenyl)ethyl]-1-methyl-3-(3-carbamoylphenyl)propylamine hydrochloride.

| Elementary Analysis | C | H | N | Cl |
|---|---|---|---|---|
| Calculated for $C_{27}H_{36}O_5N_2 \cdot HCL$ | 64.21 | 7.38 | 5.55 | 7.02 |
| Found | 63.77 | 7.38 | 5.57 | 7.21 |

PHARMACOLOGY

Example 1

The data in Table 1 were obtained from a dog anesthetized with sodium pentobarbital (30 mg/kg, i.v.). The right femoral vein was cannulated for administration of drug and the left femoral vein was used for withdrawal of blood samples. All blood samples were collected in heparinized chilled tubes. The blood was centrifuged to separate red cells and the plasma was frozen.

After obtaining a control blood sample, dobutamine infusion at the rate of 20 ug/kg/min was maintained for 30 mins. During the infusion, blood samples were drawn at 10, 20, and 30 mins. One hour after completion of the dobutamine infusion, a second control sample of blood was drawn and an infusion of Compound I at 20 ug/kg/min was begun. Samples of blood were taken during the Compound I infusion at 10, 20, and 30 mins.

The concentrations of Compound I and dobutamine in plasma were measured using HPLC with electrochemical detection. Chromatography was performed using a reverse-phase octadecylsilane ($C_{18}$) column attached to an amperometric detector equipped with a glassy carbon electrode at a potential of +600 mV. The mobile phase consisted of acetonitrile:pH 3 buffer (15:85); the buffer (pH 3) contained 0.035M $KH_2PO_4$, 0.003M citric acid and 0.002M $Na_2$ EDTA. At a flow rate of 1.5 ml/min, Compound I, dobutamine and the internal standard for the assay (dioxymethylene derivative of dobutamine) eluted in 5.4 and 7.8 min respectively.

In the assay procedure, control plasma (1 mil) spiked with 0, 20, 100, 300 and 500 ng/ml test drug was added to silanized glass tubes (13×128 mm) containing 100 ng of the internal standard as a solution in 100 ul of 5M $K_2HPO_4$. The samples were mixed and extracted twice with 4 ml of ethyl acetate. Following centrifugation, the combined organic extracts were evaporated, the residue dissolved in 200 ug of mobile phase and a 10–15 ul aliquot injected into the chromatograph. Calibration curves were constructed by plotting the peak height ratios of test drug to the internal standard over the concentration range and interpolation of unknown plasma concentrations from the fitted line.

TABLE 1

| Blood levels of Compound I and Dobutamine | | |
|---|---|---|
| Infusion Time mins. | Compound I ng/ml | Dobutamine ng/ml |
| 10 | 417 | 155 |
| 20 | 451 | 176 |
| 30 | 874 | 158 |

As shown in Table 1, the administration of Compound I gives higher blood levels than dobutamine, which helps to explain why Compound I is about ten times more potent than is dobutamine (see Table 2). The high potency of Compound I makes possible a dosage form that can be of practical size for oral or buccal administration.

Example 2

Figure 1:
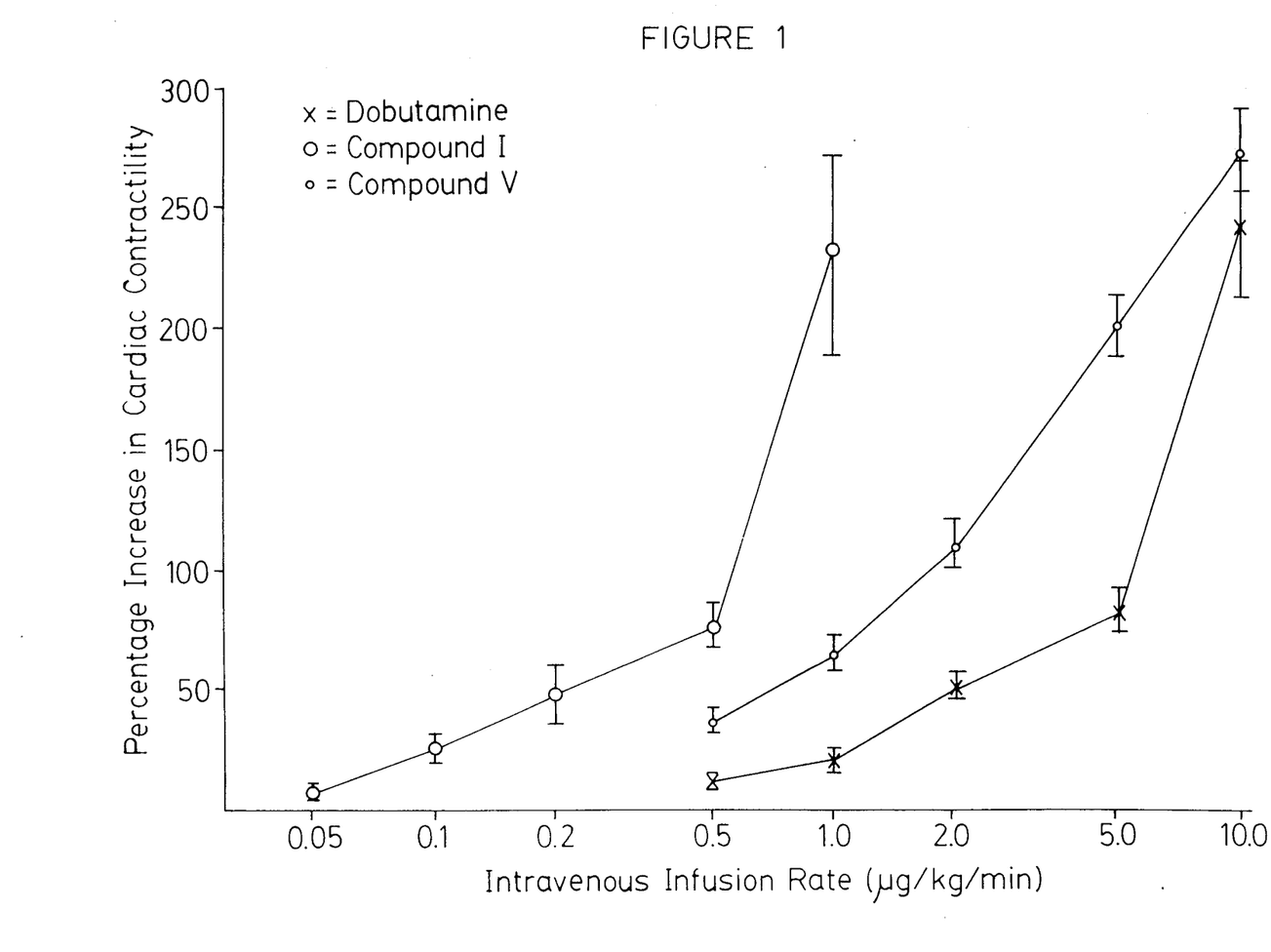
Figure 2:
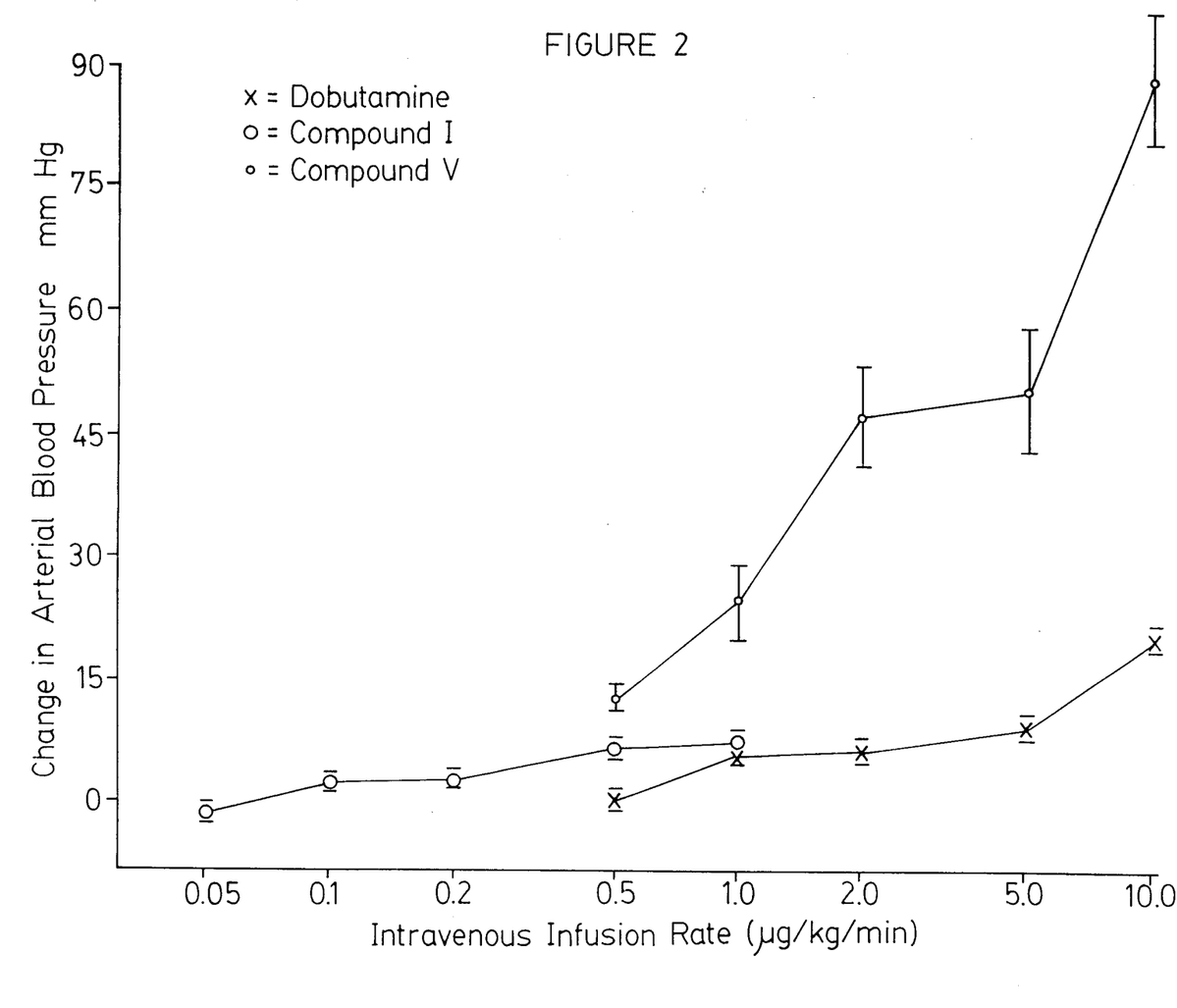

To illustrate the structural specificity of the compounds of the invention, four close structural analogs of Compound I were synthesized and their activity compared to that of Compound I. In these tests dobutamine was used as a standard so that Compound I and the four structural analogs could be compared on a common basis. FIGS. 1 and 2 graphically compares dobutamine, Compound I and Compound V (the closest structural analog of dobutamine and Compound I). Data comparing Compound I and the four analogs are given in Table 2.

The data in FIGS. 1 and 2 and Table 2 were obtained on dogs anesthetized with sodium pentobarbital (30 mg/kg, i.v.). The animals were placed on artificial respiration and the chest was opened to expose the heart. A Walton-Brodie strain gauge arch was sutured to the right ventricle for measurement of cardiac contractility. Arterial blood pressure was measured from a catheter placed in the abdominal aorta. Cardiac contractility and arterial pressure were recorded continuously on a Grass polygraph. All drugs were dissolved and infused intravenously in 0.9% NaCl solution.

The data presented demonstrates that only Compound I is both potent and lacks the undesired side effect of elevating blood pressure. Clearly then, the higher blood levels that are achieved with Compound I than with dobutamine translates into a significant advantage in potency. As shown in Table 2, a dose of Compound I about a tenth that of dobutamine is required to produce an equivalent inotropic effect. And the probability of an adverse effect of Compound I on blood pressure was no greater than that of dobutamine. Even when a dose four times greater than that required to increase cardiac contractility by 50% was given, Compound I caused no significant change in blood pressure.

A comparison of the activities of Compound I and Compound V shows that the meta position for the carbamyl group ($CONH_2$) is critical. For when the carbamyl group is in the para position, cardiac potency is less than a third of that when it is in the meta position. But even more important than the loss of potency, as shown by Table 2 and illustrated in FIG. 1, is the dangerous rise in blood pressure (FIG. 2) that occurs when the carbamyl group is para instead of meta.

A further specific structural requirement needed to meet the potency and blood pressure criteria was the 1-methyl trimethylene linkage between the amine function and phenyl ring bearing the carbamyl group. If the linkage was unbranched as in Compound III but the same chain lengths as in Compound I potency was reduced and there was an undesired elevation in blood pressure. When the linkage was shortened to ethylene, as in Compound II, there was no rise in blood pressure, but inotropic potency was not significantly better than that of dobutamine. And again, as Compound IV shows, the blood pressure side effect reappears if the carbamyl group is moved from the meta to the para position.

being administered through buccal mucosa, the device containing the drug can be readily withdrawn from the mouth. For this reason the buccal route is a preferred route of administration.

Example 4

To test the effectiveness of Compound I and its diisobutyrate ester (Compound IA) the inotropic effect after buccal administration of dobutamine, Compound

TABLE 2
The Effect of Chemical Structure on Cardiac Potency and Blood Pressure

| Compound | $R_1$ | X | $R_2$ | $R_3$ | Inotropic Potency Relative to Dobutamine Mean ± S.E. | Blood Pressure Mean ± S.E. | n |
|---|---|---|---|---|---|---|---|
| Dobutamine | $CH_3$ | 2 | H | OH | 1 | 7.8 ± 4.5 | |
| Compound I | $CH_3$ | 2 | $CONH_2$ | H | 9.1 ± 2.4 | 5.3 ± 4.5 | 6 |
| Compound II | H | 1 | $CONH_2$ | H | 1.5 ± 0.1 | −8 ± 5 | 5 |
| Compound III | H | 2 | $CONH_2$ | H | 1.4 ± 1 | 22.3 ± 16.2 | 3 |
| Compound IV | H | 1 | H | $CONH_2$ | 1.38 ± 0.2 | 26 ± 10 | 6 |
| Compound V | $CH_3$ | 2 | H | $CONH_2$ | 2.9 ± 0.3 | 49 ± ±5 | 6 |

Cardiac Potency = $\frac{CC_{50}\ Dobutamine}{CC_{50}\ Test\ Compound}$ $CC_{50}$ = the intravenous infusion rate that increases cardiac contractility by 50%
Blood Pressure = change in diastolic blood pressure caused by a dose 4 times larger than $CC_{50}$
n = number of dogs

Example 3

Figure 3:
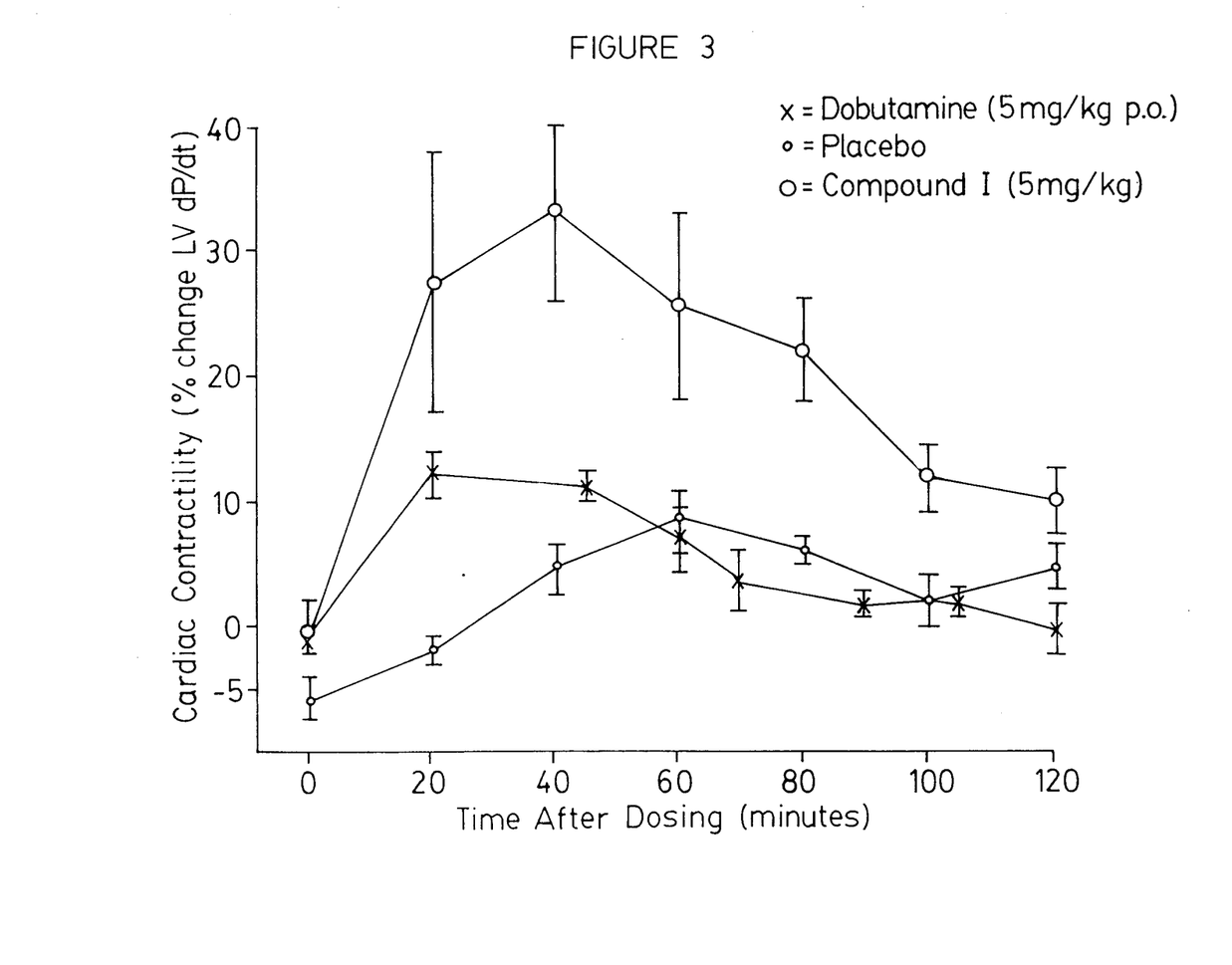

To test the effectiveness of Compound I when swallowed, five previously trained dogs, instrumented with a miniature pressure transducer for measurement of cardiac contractility were used. On different days the conscious dogs were tested with placebo, dobutamine (5 mg/kg) or Compound I (5 mg/kg). As illustrated in FIG. 3, dobutamine did not produce a response significantly better than the placebo. In contrast to dobutamine, Compound I produced a strong inotropic response persisting for more than two hours.

Several months prior to doing the procedure described above, a minature pressure transducer was mounted in the left ventricle of each dog's heart. The dogs were trained to swallow capsules and lie quietly for up to 3 hours. During this time, continuous recording of left ventricular pressure was made on a Grass polygraph. Also recorded was an electronically differentiated signal on the left ventricular pressure. This differential is referred to as LV dP/dt. This LV dP/dt is the rate that the left ventricle develops pressure and is accepted as an index of cardiac contractility.

On each day of testing the dogs were forced to swallow a gelatin capsule that was either empty (placebo), or contained dobutamine (5 mg/kg) or Compound I (5 mg/kg). Recordings were then made of cardiac contractility for 2 hours after the dog swallowed the capsule.

The above results showed that Compound I was effective when swallowed, but this route of administration is not as safe as the buccal route. Although Compound I would share with dobutamine low potential for causing cardiac arrhythmia or angina (in ischemic heart disease), an overdose could precipitate these side effects. If either side effect occurs after the drug is swallowed, the drug can't be removed from the body; one can only wait for the drug to wear off. On the other hand, if undesired side effects occur while the drug is

I, Compound I-A, the dipivalyl ester of Compound I (Compound I-B), and the diisobutyrate ester derivative of Compound V (Compound V-A) were compared in 19 anesthetized dogs. The dogs were anesthetized with sodium pentobarbital as described above and a Millar ® transducer-tip catheter positioned in the left ventircle after introduction through the left carotid artery. Left ventricular pressure was obtained from this catheter and electronically differentiated to obtain dP/dt.

The dogs were placed on their backs, and their heads and noses positioned so that their hard palates were level. After an appropriate period to collect control dP/dt values, the test drug was applied to the hard palate. The test drugs were made up in a solution of 50% ethanol in distilled water adjusting concentrations so that the desired dose was contained in 2.5 ml of solution. The drug solution was applied to a 100 mm² area of the hard palate contained by fitting parafilm over the drug solution lying on the palate.

Figure 4:
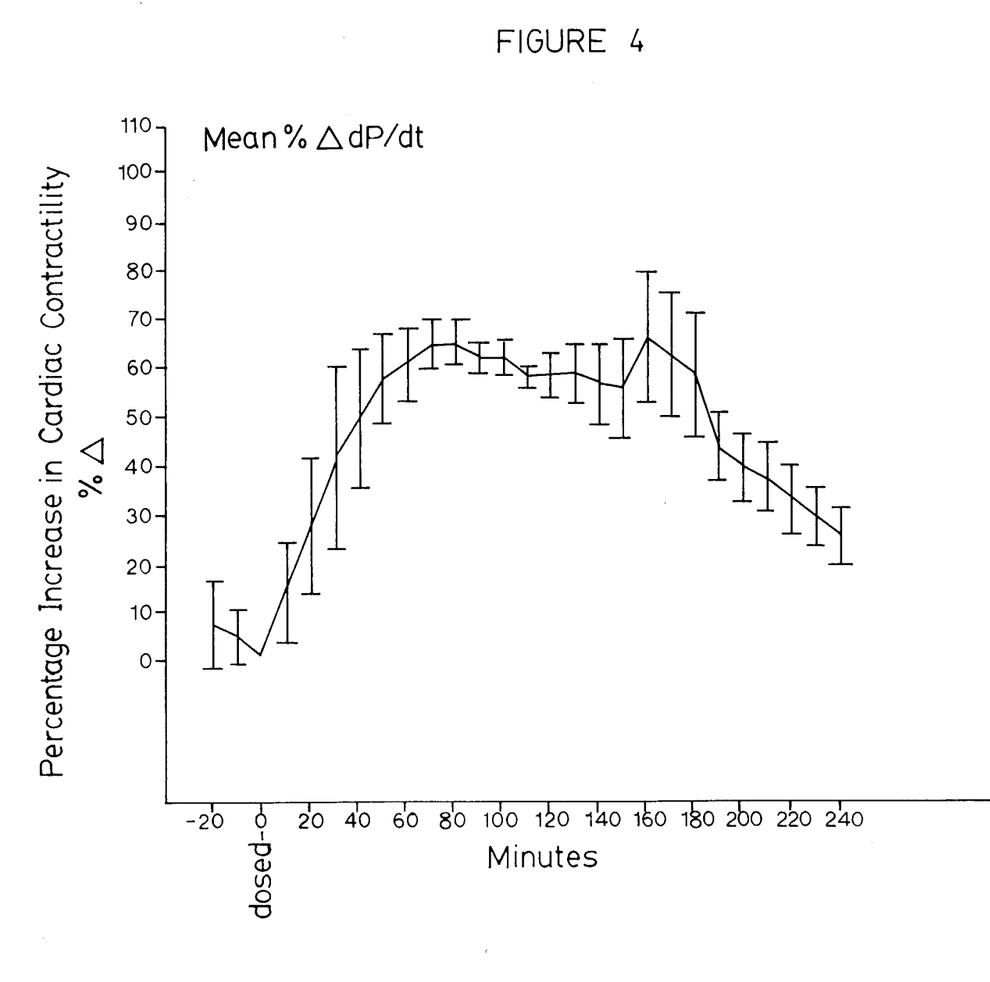

FIG. 4 illustrates the effectiveness of Compound I-A by this route. In contrast to the effectiveness of the diisobutyric ester of Compound I, the dipivalyl ester (Compound I-B) produced a small response. And as shown in Table 3, the diisobutyrate ester of Compound V (V-A) gave no response.

| Compound | R | X | Y |
|---|---|---|---|
| I-A | $(CH_3)_2CH-$ | $CONH_2$ | H |
| I-B | $(CH_3)_3C-$ | $CONH_2$ | H |

-continued

| Compound | R | X | Y |
|---|---|---|---|
| V-A | (CH₃)₂CH | H | CONH₂ |

TABLE 3

The inotropic response produced by buccal administration of compounds I, I-A, I-B, V-A and dobutamine

| Compound | Dose mg/kg | Inotropic Response* Percent Change from Control Mean ± S.E. | n** |
|---|---|---|---|
| I | 2 | 16.6 ± 6 | 4 |
| I-A | 1.39 | 61 ± 3 | 4 |
| I-B | 1.39 | 13 ± 7 | 3 |
| V-A | 1.39 | No response | 2 |
| Dobutamine | 5 | 2.7 ± 2 | 6 |

*Peak change in left ventricular dP/dt.
Control = dP/dt prior to applying drug to buccal mucosa.
**The number of dogs used for each test.

As seen by the summary of results given in Table 3, it is clear that Compound I-A was the most effective by this route. Note that a dose of 1.39 mg/kg of the diisobutyrate ester derivative (Compound I-A) produced a greater response than did 2 mg/kg of the parent Compound I. On a molar basis, 1.39 mg of Compound I-A equals one half of the 2 mg dose of Compound I. Thus, in these tests, Compound I-A was more than twice as potent as Compound I.

Example 5

The degree to which the diisobutyrate ester displays enhanced buccal absorption can be seen by comparing the doses of Compound I and Compound I-A required to produce an equivalent inotropic effect when given intravenously to two anesthetized dogs as shown in Table 4.

TABLE 4

Intravenous infusion rates (ug/kg/min) of Compounds I and I-A required to increase cardiac contractility by 50%

| | | Dose Ratio |
|---|---|---|
| Dog #1 | Compound I-A = 2.8 | 9.6 |
| | Compound I = 0.29 | |
| Dog #2 | Compound I-A = 1.25 | 12.9 |
| | Compound I = 0.097 | |

When given by intravenous infusion, the diisobutyrate ester (Compound I-A) was more than nine times less potent than the parent catechol (Compound I). Yet by the buccal route of administration, the ester was more than twice as potent as its parent. Therefore, the ester derivative was better absorbed through the buccal mucosa by a factor of more than eighteen times than was the parent compound.

Such better absorption means that the diisobutyrate ester derivative will be more reliably and consistently absorbed than the parent compound. Reliability and consistency of dosing are of paramount importance when using a powerful inotropic drug to treat patients with heart disease. For these reasons Compound I-A is the preferred compound for the buccal route.

I claim:

1. A compound of the formula where R is hydrogen or isobutyrate, or a pharmaceutically acceptable acid addition salt thereof.

2. A compound according to claim 1, wherein R is hydrogen.

3. A compound according to claim 1, wherein R is isobutyrate.

4. A compound according to claim 1, N-[2-(3,4-dihydroxyphenyl)ethyl]-1-methyl-3-(3-carbamoylphenyl)-propylamine hydrochloride.

5. A compound according to claim 1, N-[2-(3,4-diisobutyryl oxyphenyl)ethyl]-1-methyl-3-(3-carbamoylphenyl)propylamine hydrochloride.

6. A method for increasing cardiac contractility in a warm-blooded animal suffering from depressed cardiac contractility which comprises administering to said animal an effective amount of a compound of the formula wherein R is hydrogen or isobutyrate, or a pharmaceutically acceptable acid addition salt thereof.

7. A method according to claim 6, wherein R is hydrogen and the compound is administered orally.

8. A method according to claim 6, wherein R is isobutyl and the compound is administered buccally.

9. A method according to claim 6, wherein R is hydrogen and the compound is administered intravenously.

10. A method according to claim 6, wherein R is isobutyl and the compound is administered orally.

11. A pharmaceutical composition in dosage unit form which comprises a dosage effective for the treatment of depressed cardiac contractility of a compound of the formula or a pharmaceutically acceptable salt thereof, and a pharmaceutically acceptable carrier.

12. A pharmaceutical composition in dosage unit form which comprises a dosage effective for the treatment of depressed cardiac contractility of a compound of the formula or a pharmaceutically acceptable salt thereof, and a pharmaceutically acceptable carrier.

* * * * *